US012751703B2

(12) United States Patent
Sharma et al.

(10) Patent No.: US 12,751,703 B2
(45) Date of Patent: Oct. 6, 2026

(54) MEDICAL SYSTEMS, DEVICES, AND RELATED METHODS THEREOF

(71) Applicants: Boston Scientific Scimed, Inc., Maple Grove, MN (US); Boston Scientific Medical Device Limited, Galway (IE)

(72) Inventors: Deepak Kumar Sharma, Muzaffarnagar (IN); Rajivkumar Singh, Thane (IN); Sharath Kumar G, Kanakapura (IN); Paul Smith, Smithfield, RI (US)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 194 days.

(21) Appl. No.: 18/486,258

(22) Filed: Oct. 13, 2023

(65) Prior Publication Data

US 2024/0122588 A1 Apr. 18, 2024

Related U.S. Application Data

(60) Provisional application No. 63/416,054, filed on Oct. 14, 2022.

(51) Int. Cl.
*A61B 17/00* (2006.01)

(52) U.S. Cl.
CPC *A61B 17/0057* (2013.01); *A61B 2017/00004* (2013.01); *A61B 2017/00238* (2013.01); *A61B 2017/00296* (2013.01); *A61B 2017/00314* (2013.01); *A61B 2017/00323* (2013.01); *A61B 2017/00367* (2013.01); *A61B 2017/00592* (2013.01); *A61B 2017/0061* (2013.01); *A61B 2017/00623* (2013.01); *A61B 2017/0065* (2013.01); *A61B 2017/00681* (2013.01); *A61B 2017/00818* (2013.01);

(Continued)

(58) Field of Classification Search
None
See application file for complete search history.

(56) References Cited

U.S. PATENT DOCUMENTS 5,336,227 A * 8/1994 Nakao .................... A61B 18/14
606/113
2009/0264919 A1* 10/2009 Sater .................. A61B 17/0057
606/213

(Continued)

FOREIGN PATENT DOCUMENTS

EP 2 108 315 B1 9/2017

OTHER PUBLICATIONS

International Search Report of PCT/US2023/076770, mailed Jan. 16, 2024.

*Primary Examiner* — Mohamed G Gabr
(74) *Attorney, Agent, or Firm* — Bookoff McAndrews, PLLC

(57) ABSTRACT

A medical device, comprising a handle, wherein the handle includes a movable body and a stationary body; an end cap, the end cap comprising an inner cap and an outer cap, wherein the inner cap is coupled to the movable body by a control element such that movement of the movable body relative to the stationary body extends the inner cap relative to the outer cap; and a patch disposed between the inner cap and the outer cap such that movement of the inner cap relative to the outer cap at least partially deploys the patch.

20 Claims, 10 Drawing Sheets

(52) U.S. Cl.
CPC ............... *A61B 2017/00862* (2013.01); *A61B 2017/00867* (2013.01); *A61B 2017/00884* (2013.01); *A61B 2017/00902* (2013.01); *A61B 2017/00951* (2013.01); *A61B 2017/00991* (2013.01); *A61B 2560/0406* (2013.01)

(56) References Cited

U.S. PATENT DOCUMENTS

| | | | | |
|---|---|---|---|---|
| 2017/0172602 | A1* | 6/2017 | Carrillo, Jr. ........ | A61B 18/1492 |
| 2020/0038005 | A1* | 2/2020 | Smith .................... | A61L 24/08 |
| 2021/0401416 | A1 | 12/2021 | King | |
| 2022/0265968 | A1* | 8/2022 | Whelehan ......... | A61M 25/0155 |

* cited by examiner

MEDICAL SYSTEMS, DEVICES, AND RELATED METHODS THEREOF

CROSS-REFERENCE TO RELATED APPLICATIONS

This application claims the benefit of priority of U.S. Provisional Patent Application No. 63/416,054, filed on Oct. 14, 2022, the entirety of which is incorporated herein by reference.

TECHNICAL FIELD

The disclosure relates generally to medical systems, devices, and related methods for delivering patches. More specifically, at least certain embodiments of the disclosure relate to systems, devices, and/or methods for delivering patches, for example, for hemostasis, among other aspects.

BACKGROUND

Technological developments have given users of medical systems, devices, and methods the ability to conduct increasingly complex procedures on subjects. One challenge in the field of minimally invasive surgeries is associated with preventing or stopping a bleed, such as, for example, a bleeding ulcer, within a lumen, organ, or cavity of a subject. Common treatments for bleeding ulcers include, for example, injection therapies, thermal therapies, mechanical therapies, and hemostatic powders. Such therapies are often expensive and/or time-consuming. Furthermore, such therapies may not be able to treat a larger surface area, for example, a larger bleed in the gastrointestinal (GI) tract. Additionally, a common treatment for chronic ulcers is a gastric bypass. Such procedures may be more difficult, more time-consuming, more costly, and/or less effective/accurate than a minimally-invasive procedure to position a patch on one or more bleeds. Therefore, a need exists for systems, devices, and/or methods for positioning and/or deploying one or more hemostatic patches on one or more portions of a subject.

SUMMARY

This disclosure includes medical systems and devices comprising a biocompatible patch and methods of use thereof, e.g., methods of delivering a patch to a treatment site of a patient, for example, to help treat an ulcer and/or to perform hemostasis. Each of the examples disclosed herein may include one or more of the features described in connection with any of the other disclosed examples.

According to one aspect, a medical device may comprise a handle, an end cap, and a patch. The handle may include a movable body and a stationary body. The end cap may comprise an inner cap and an outer cap. The inner cap may be coupled to the movable body by a control element such that movement of the movable body relative to the stationary body extends the inner cap relative to the outer cap. The patch may be disposed between the inner cap and the outer cap such that movement of the inner cap relative to the outer cap at least partially deploys the patch.

Any of the examples described herein may have any of the following features in any combination. The medical device may further comprise a support structure partially surrounding a portion of the inner cap, and distal movement of the inner cap relative to the outer cap may result in the support structure expanding. The support structure may include a woven shape-memory material.

The inner cap may include a proximal wall and a distal wall extending radially outward from the inner cap. In a first configuration, an outer edge of the distal wall of the inner cap may abut an inner edge of the outer cap, and, in a second configuration, the outer edge of the distal wall of the inner cap may be distal to the inner edge of the outer cap.

The control element may be moveably disposed within a lumen of a sheath. The sheath may be coupled to the outer cap. The end cap may be removably coupled to an endoscope by one or more fasteners, adhesives, or a friction fit. The inner cap may include a lumen extending from a proximal end to a distal end. The patch may include an adhesive on a side of the patch facing away from inner cap. At least a portion of the end cap may be transparent.

According to an alternative aspect, a medical device may comprise an end cap, an expandable structure, and a patch. The end cap may comprise an inner cap and an outer cap. The expandable structure may partially surround a portion of the inner cap. The patch may be positioned around the expandable structure. In a first configuration, the inner cap may be disposed within the outer cap and the patch may be disposed between a portion of the inner cap and a portion of the outer cap. In a second configuration, at least a portion of the inner cap may be distal to the outer cap and the patch may be released.

Any of the examples described herein may have any of the following features in any combination. The medical device may further comprise a coupler ring coupled to a proximal face of the end cap by one or more sheaths. The end cap may be movable relative to the coupler ring. The support structure may include a woven shape-memory material. The inner cap may include a proximal wall and a distal wall extending radially outward from the inner cap. In a first configuration, an outer edge of the distal wall of the inner cap may abut an inner edge of the outer cap. In a second configuration, the outer edge of the distal wall of the inner cap may be distal to the inner edge of the outer cap. In a third configuration, the end cap may be distal to a distal end of an endoscope. At least a portion of the end cap may be transparent. The inner cap may include a lumen extending from a proximal end of the inner cap to a distal end of the inner cap.

Aspects of this disclosure also include reference to an exemplary method. The method may comprise delivering a medical system to a treatment site, extending the inner cap relative to the outer cap by moving the movable body relative to the stationary body, and releasing the patch. The medical system may comprise a scope and a medical device. The medical device may comprise a handle having a movable body and a stationary body, an end cap removably coupled to a distal end of the scope, an expandable structure at least partially surrounding a portion of the inner cap, and a patch disposed between the inner cap and the outer cap. The end cap may comprise an inner cap and an outer cap. The inner cap may be coupled to the movable body of the handle by one or more control elements.

The method may further comprise, before extending the inner cap relative to the outer cap, manipulating one or more portions of the handle to extend the end cap from the distal end of the scope.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to aspects of this disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Although the treatment site is discussed herein as being in the subject's GI tract, this disclosure is not so limited, as the treatment site may be any internal lumen, organ, cavity, or other tissue within the subject. Additionally, although endoscopes are referenced herein, it will be appreciated that the disclosure encompasses any medical devices having a working channel extending from a proximal end to a distal end, such as ureteroscopes, duodenoscopes, gastroscopes, endoscopic ultrasonography ("EUS") scopes, colonoscopes, bronchoscopes, laparoscopes, arthroscopes, cystoscopes, aspiration scopes, sheaths, or catheters.

Embodiments of the disclosure may solve one or more of the limitations in the art. The scope of the disclosure, however, is defined by the attached claims and not the ability to solve a specific problem.

Figure 1:
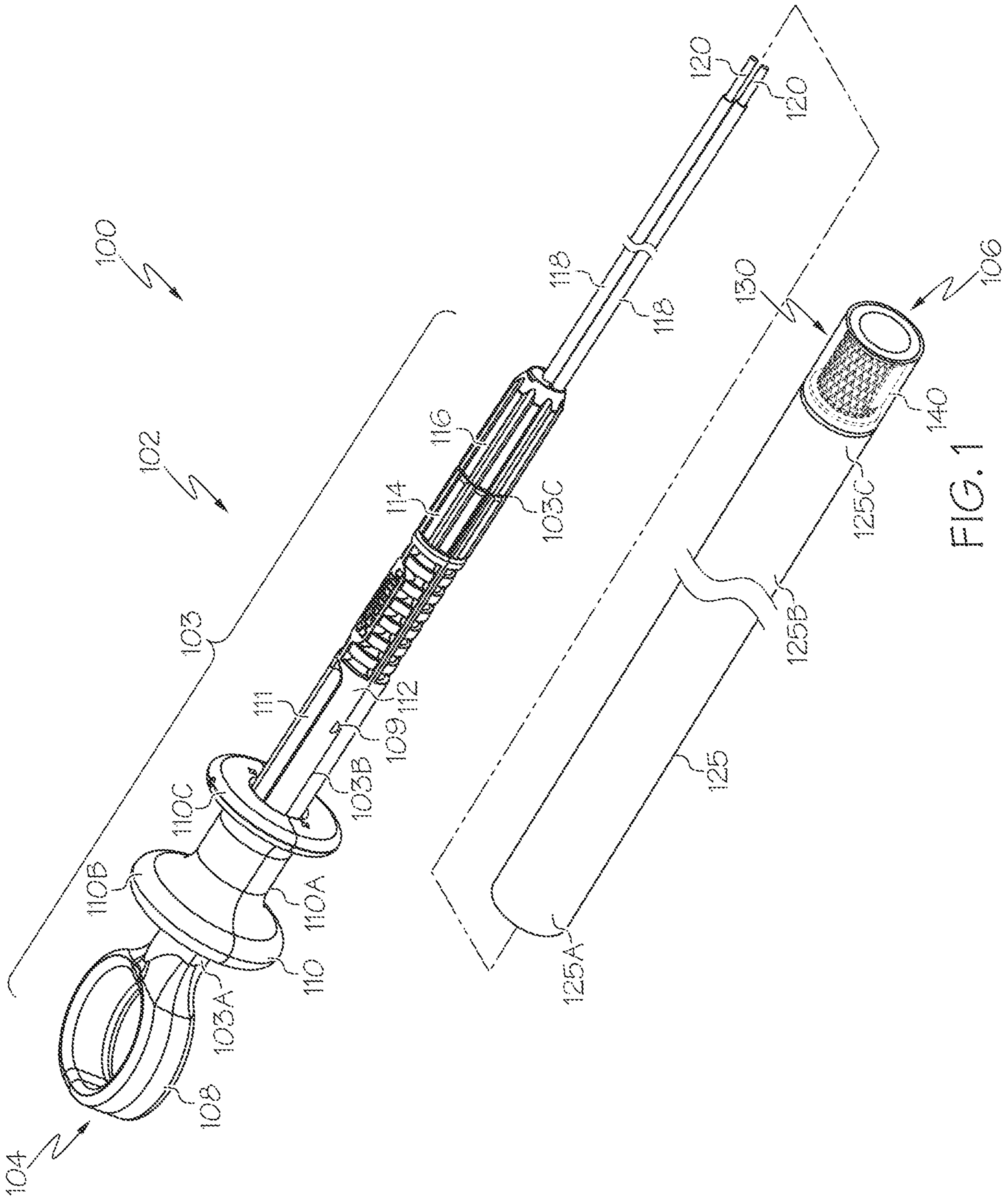
FIG. 1 is a perspective view of an exemplary medical system, including an exemplary medical device and a portion of an endoscope, according to aspects of this disclosure.

FIG. 1 depicts a perspective view of a medical system 100, for example, including a medical device 102 and an endoscope 125. As discussed in detail herein, medical device 102 may include a handle 103 and an end cap 130. End cap 130 may be coupled to a distal end 106 of medical device 102. A patch 140 may be positioned within or internal to one or more portions of end cap 130 during the delivery of endoscope 125 and end cap 130 to a treatment site. For example, end cap 130 of medical device 102 may be coupled to a distal portion 125C (e.g., a distal end) of endoscope 125. End cap 130 may be coupled to endoscope 125 before insertion of endoscope 125 into the subject, such that end cap 130 and distal portion 125C of endoscope 125 may be delivered to the treatment site. Then, the user may manipulate one or more portions of handle 103 to control (e.g., extend or retract) one or more portions of end cap 130 to position and/or deploy patch 140. Furthermore, although not shown, endoscope 125 may include one or more proximal controls (dials, levers, buttons, etc.), for example, to extend or retract, deflect, or otherwise control the position of distal portion 125C of endoscope 125, and thus control the position of end cap 130 before the positioning and/or deployment of patch 140.

As mentioned, a proximal end 104 of medical device 102 may include handle 103. Handle 103 may include a proximal handle portion 103A, an intermediate handle portion 103B, and a distal handle portion 103C. Proximal handle portion 103A may include a finger ring 108, for example, to receive the user's thumb. Specifically, finger ring 108 may be positioned on a proximal end of proximal handle portion 103A. Distal handle portion 103C may include a first portion 114 and a second portion 116, which may include one or more ridges or indentations, for example, to facilitate a user's grip on handle 103.

Handle 103 additionally includes a first, or movable, body 110 and a second, or stationary, body 112. For example, movement of movable body 110 relative to stationary body 112 may control the movement (e.g., extension or retraction) of one or more control element(s) 120, for example, control wire(s), and thus control element(s) 120 may control the movement (e.g., extension or retraction) of one or more portions of end cap 130. Movable body 110 may partially surround a portion of stationary body 112, and a portion of movable body 110 may at least partially extend into a handle slot 111. Handle slot 111 may extend longitudinally through at least a portion of stationary body 112 of handle 103. In some aspects, although not shown, handle 103 may include one or more biasing elements (e.g., one or more springs), for example, such that distal movement of movable body 110 relative to stationary body 112 is biased proximally. In these aspects, when the user releases a distal pressure or force on movable body 110, the one or more biasing elements may bias movable body 110 proximally, for example, to the position shown in FIG. 1. Moreover, at least a portion of movable body 110 may be coupled to (e.g., directly or indirectly) or otherwise connected to control element(s) 120.

Movable body 110 may include one or more reduced diameter sections or grooves 110A, for example, between a proximal ridge 110B and a distal ridge 110C, which may help to facilitate the user's grip of movable body 110. For example, the user may place movable body 110 between two fingers such that the user's fingers are positioned within groove 110A. Accordingly, movement of the user's fingers (i.e. relative to the user's thumb in finger ring 108) controls the position of movable body 110 relative to stationary body 112, and thus the movement of control element(s) 120 and/or one or more portions of end cap 130.

In some aspects, stationary body 112 (e.g., a portion of intermediate handle portion 103B of handle 103) and/or movable body 110 may include one or more visual or physical indicator(s) 109. Indicator(s) 109 may include, for example, indentations, raised surfaces, markings, etc. Indicator(s) 109 may physically or visually indicate the actuation or extension of end cap 130. For example, as movable body 110 is advanced distally relative to stationary body 112, thus actuating end cap 130, movable body 110 may have to overcome, for example, indicator(s) 109. Indicator (s) 109 may signal to the user that end cap 130 has been actuated, or is in an extended position. Additionally or alternatively, the user may utilize markings on handle 103 or other visual indicators to determine a status, position, actuation status, etc. of one or more portions of end cap 130.

Still referring to FIG. 1, endoscope 125 may include a generally cylindrical tubular shape, and may include a proximal portion 125A, distal portion 125C, and an intermediate portion 125B. Although not shown, proximal portion 125A may include or otherwise be coupled to a handle, for example, including one or more ports, controls, levers, buttons, electrical communication connections, etc. Additionally, endoscope 125 may include one or more lumen(s) 127 (shown in FIG. 2B) or working channels. Lumen(s) 127 may extending longitudinally through endoscope 125, for example, extending through proximal portion 125A, intermediate portion 125B, and distal portion 125C.

Endoscope 125 (i.e., distal portion 125C of endoscope 125) may include an outer diameter of approximately 9 millimeters to approximately 20 millimeters, for example, approximately 10.5 millimeters to approximately 12 millimeters. As mentioned, endoscope 125 may include lumen(s) 127, for example, a working channel with a diameter of approximately 2 millimeters to approximately 4 millimeters, for example, approximately 2.8 millimeters. One or more lumen(s) 127 may terminate at a distal face 125D of endoscope 125. Additionally, as shown in FIG. 2B, distal face 125D of endoscope 125 may include one or more illumination device(s) 128 (e.g., one or more LEDs, optical fibers, and/or other illuminators). Distal face 125D may additionally or alternatively include one or more visualization device (s) 129 (e.g., one or more cameras, one or more image sensors, endoscope viewing elements, optical assemblies, including one or more image sensors and one or more lenses, etc.).

As shown in FIG. 1, when medical device 102, including end cap 130, is coupled to endoscope 125 (i.e. during delivery and positioning), end cap 130 and/or a distal portion of medical device 102 may be coupled to distal portion 125C of endoscope 125. For example, distal portion of medical device 102 and/or a proximal portion of end cap 130 may be attached to an external surface of distal portion 125C of endoscope 125. For example, the proximal portion of end cap 130 may include an internal diameter that is complementary to and may receive an exterior diameter of endoscope 125. End cap 130 may be attached to distal portion 125C of endoscope 125 by methods of, for example, an adhesive, a mechanical fit, a snap fit, a press fit, a weld, or any other coupling techniques commonly known in the art. Additionally or alternatively, end cap 130 may be coupled to and/or extend distally beyond the distal opening(s) of lumen (s) 127 (shown in FIG. 2B). Although not shown, a portion of end cap 130 may extend proximally into one or more lumen(s) 127 and couple to an internal surface within one or more lumen(s) 127 via, for example, an adhesive, a mechanical fit, a snap fit, a press fit, a weld, or any other coupling techniques commonly known in the art.

To provide additional stability of medical device 102 relative to endoscope 125, one or more portions of medical device 102 may also be coupled to endoscope 125 elsewhere along the longitudinal length of endoscope 125. For example, a proximal portion of one or more sheath element (s) 118 and/or an intermediate portion of sheath element(s) 118 may be coupled to, for example, proximal portion 125A, and/or intermediate portion 125B, respectively, of endoscope 125. One or more portions of handle 103 may additionally or alternatively be coupled to one or more portions of endoscope 125, such as, for example at a handle (not shown) of endoscope 125.

Although not shown, endoscope 125 may include one or more grooves, channels, lumens, and/or other features to movably receive control element(s) 120 and/or sheath element(s) 118 of medical device 102. The one or more grooves, channels, lumens, and/or other features may at least partially extend internally (e.g., on an internal surface) or externally (e.g., on an external surface) along a longitudinal length of endoscope 125. Alternatively or additionally, system 100 could include an outer sheath (not shown) to assist with encapsulating endoscope 125, sheath element(s) 118 and/or control element(s) 120. Furthermore, although not shown, one or more portions of endoscope 125 (e.g., distal portion 125C) may be deflectable, for example, via one or more knobs, levers, buttons, or other controls on a proximal handle. In these aspects, distal portion 125C of endoscope 125 may be maneuvered while being delivered to the treatment site and/or positioned relative to the treatment site, for example, in a retroflex position, which may be used when the treatment site is in the subject's esophagus, stomach, duodenum, colon, or other portion of the GI tract. Accordingly, at least portions of medical device 102 may be flexible or semi-flexible, for example, in order to be maneuvered along with endoscope 125.

Referring still to FIG. 1, control element(s) 120 may extend from one or more portions of handle 103 of medical device 102 to one or more portions of end cap 130. Control element(s) 120 may each be formed by a wire, a coil, a tube, etc. Additionally, one or more sheath element(s) 118 may extend from one or more portions of handle 103 to one or more portions of end cap 130. Sheath element(s) 118 may each be formed by a coil, a tube, a sheath, etc., and may have an internal lumen (not shown) extending longitudinally to receive control element(s) 120. In these aspects, each control element 120 may be radially within a respective sheath element 118 (e.g., control element 120 may be moveably disposed within a lumen of sheath element 118).

Sheath element(s) 118 and/or control element(s) 120 may extend externally to endoscope 125 (e.g., along an external surface of endoscope 125). In such an instance, end cap 130 may be fixedly or removably coupled to control element(s) 120. End cap 130 may be fixedly or removably coupled to control element(s) 120 by techniques such as, for example, an adhesive, a mechanical fit, a snap fit, a press fit, a friction fit, a weld, or any other techniques or fasteners commonly known in the art. Any combination of techniques for coupling end cap 130 to control element(s) 120 is also permissible (e.g., an adhesive and a snap fit).

Alternatively, sheath element(s) 118 and/or control element(s) 120 may extend through lumen(s) 127 of endoscope 125. In such an instance, end cap 130 may be removably coupled to control element(s) 120 to enable the user to introduce sheath element(s) 118 through lumen(s) 127 of endoscope 125. In alternative configurations, end cap 130 may be fixedly coupled to control element(s) 120 and control element(s) may be removably coupled to handle 103.

Figure 2A:
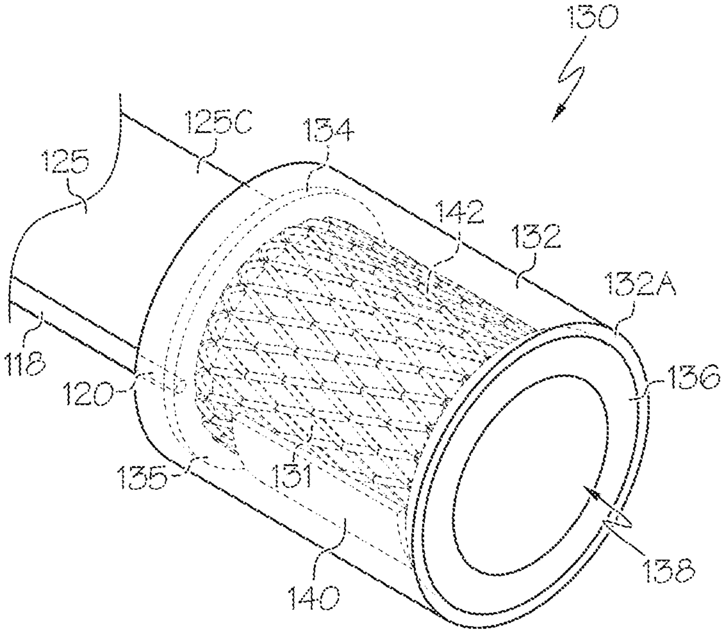
FIG. 2A is a perspective view of a portion of a distal end of the medical device of FIG. 1 coupled to a distal end of the endoscope, according to aspects of this disclosure.
Figure 2B:
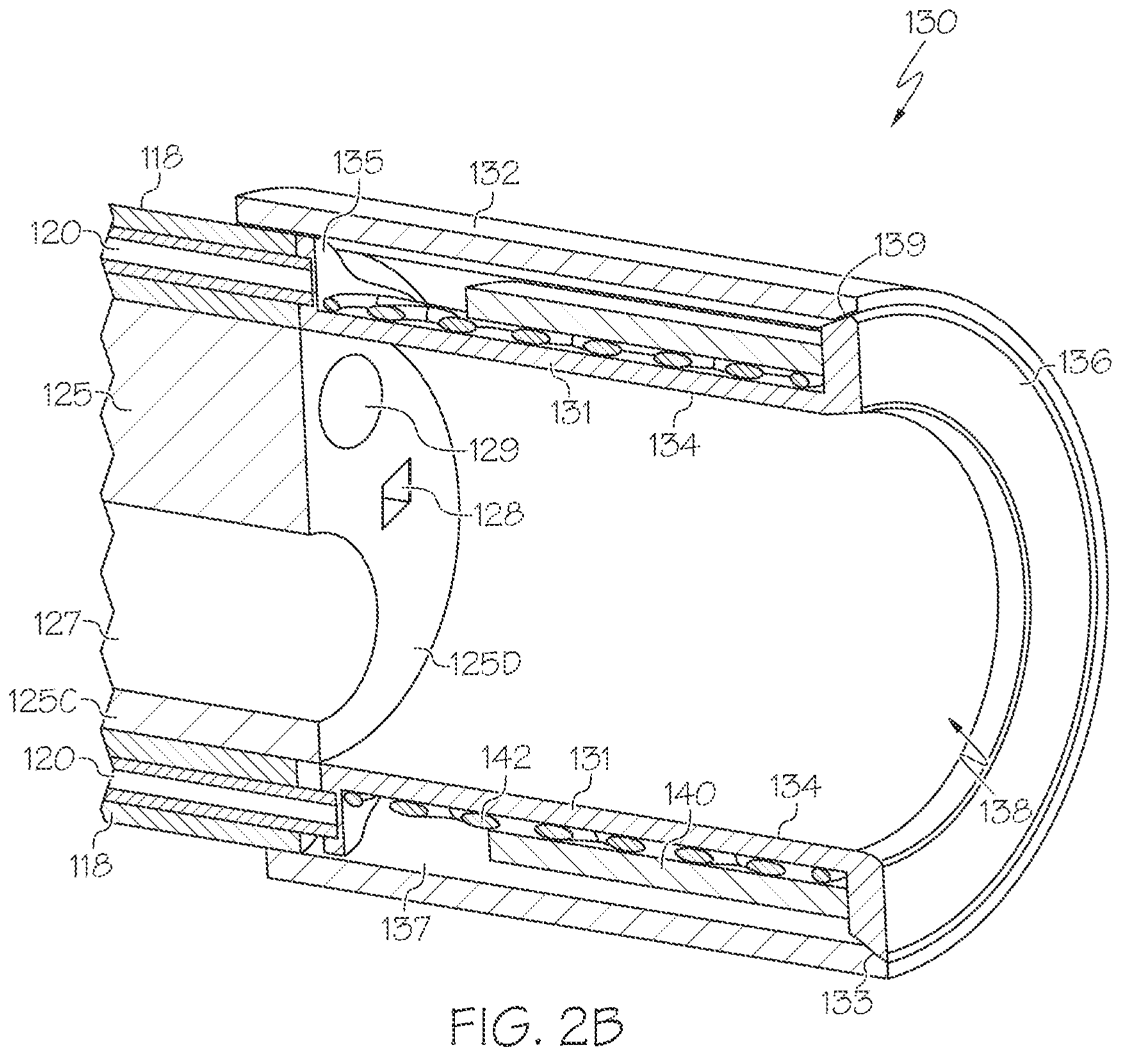
FIG. 2B is a cross-sectional view of the distal end shown in FIG. 2A, according to aspects of this disclosure.

FIGS. 2A and 2B are different views of end cap 130 in a first (e.g., retracted) configuration. Specifically, FIG. 2A is a perspective view of end cap 130 in the first configuration, and FIG. 2B is a cross-sectional view of end cap 130 in the first configuration. End cap 130 may be in the first configuration during, for example, the delivery of endoscope 125 and end cap 130 to the treatment site. End cap 130 may be coupled to distal portion 125C of endoscope 125, as previously described. End cap 130 may include a generally cylindrical shape (as shown in FIGS. 1, 2A, and 2B), though it is understood that other shapes (e.g., ovular, square, rectangular, etc.) may be utilized. In some aspects, the shape of end cap 130 may correspond to the shape of distal portion 125C of endoscope 125.

End cap 130 further comprises an inner cap 134 and an outer cap 132. Patch 140, to be described in further detail below, may be positioned within outer cap 132, for example, on an external surface of a support structure 142 surrounding an intermediate portion 131 of inner cap 134. Inner cap 134 may include intermediate portion 131 extending between a proximal wall 135 and a distal wall 136. Proximal wall 135 and distal wall 136 may project radially outward from intermediate portion 131. Support structure 142 may extend between a distal face of proximal wall 135 to a proximal face of distal wall 136 and at least partially surround intermediate portion 131. Additionally, a lumen 138 extends from a proximal end to a distal end of inner cap 134. As shown in FIG. 2B, an outer edge 133 of distal wall 136 may be formed, such that inner cap 134 is more easily accepted by outer cap 132. For example, outer edge 133 may be rounded, chamfered, or beveled. Outer edge 133 may help to form a stop surface, for example, when inner cap is retracted proximally. Outer edge 133 may alternatively form a gradual stop surface.

Support structure 142 may comprise any device having expandable and/or shape-memory characteristics, such as, for example, a stent. Accordingly, support structure 142 may be formed of one or more flexible or semi-flexible materials, for example, including expandable and/or shape-memory characteristics, such as, for example, plastic, Nitinol, cobalt Nitinol, stainless steel, or any material(s) commonly known in the art. The one or more materials may, for example, be woven or intertwined around intermediate portion 131. Additionally or alternatively, the one or more materials may form wires extending longitudinally and/or laterally between proximal wall 135 and distal wall 136. In either instance, in the first configuration, support structure 142 may be positioned between proximal wall 135 and distal wall 136 in an unexpanded state, for example, such that an internal surface of support structure 142 abuts a radial external surface of intermediate portion 131.

Control element(s) 120 may be coupled to a proximal portion of inner cap 134, for example, to a proximal face of proximal wall 135. Additionally or alternatively, control element(s) 120 may extend into a proximal portion of proximal wall 135, as shown in FIG. 2B, for example, to further secure control element(s) 120 to inner cap 134. Control element(s) 120 may be coupled to inner cap by methods of, for example, an adhesive, a mechanical fit, a snap fit, a press fit, a weld, or any other coupling techniques commonly known in the art. As shown in FIG. 2B, one or more sheath element(s) 118 may be coupled to outer cap 132. For example, an external surface of sheath element(s) 118 may be coupled to an internal surface of outer cap 132. Sheath element(s) 118 may be coupled to the internal surface of outer cap 132 by methods of, for example, an adhesive, a mechanical fit, a snap fit, a press fit, a weld, or any other coupling techniques commonly known in the art. Coupling sheath element(s) 118 to outer cap 132 and control element(s) 120 to inner cap 134 may enable the user to extend inner cap 134 distally from outer cap 132 and/or retract inner cap 134 proximally relative to outer cap 132. For example, sheath element(s) 118 (and thus outer cap 132) may remain stationary as control element(s) 120 (and thus inner cap 134) extend distally or retract proximally.

Outer cap 132 further comprises a lumen 137, shown in FIG. 2B, for receiving inner cap 134. For example, in the first configuration, inner cap 134 is positioned within lumen 137 of outer cap 132, for example, such that a distal face of a distal wall 136 of inner cap 134 is adjacent or proximal to a distal end 132A of outer cap 132. Additionally, in such a configuration, a proximal face of a proximal wall 135 of inner cap 134 is adjacent or distal to a proximal face of outer cap 132. As shown in FIG. 2B, an inner edge 139 of outer cap 132 may be formed to more easily accept inner cap 134. For example, inner edge 139 may be rounded, chamfered, or beveled. Alternatively or additionally, one or more surfaces of inner edge 139 may be complementary to outer edge 133 of distal wall 136 of inner cap 134. For example, outer edge 133 may abut, or touch, inner edge 139 in the first configuration. Inner edge 139 may, for example, gradually abut outer edge 133 when inner cap 134 is retracted. As outer edge 133 abuts inner edge 139, the user may experience tactile feedback on the handle. For example, when manipulating movable body 110, the user may experience an abrupt stop or feel an increase in frictional forces as outer edge 133 abuts inner edge 139.

Outer cap 132 and inner cap 134 may each be formed of a rigid or semi-rigid material (e.g. stainless steel, titanium, polypropylene plastic, high-density polyethylene plastic, acrylic, glass, etc.) In some embodiments, one or more portions (e.g., distal portions) of outer cap 132 and/or inner cap 134 may be transparent or at least partially transparent. In these aspects, outer cap 132 and/or inner cap 134 may not substantially interfere with visualization device(s) 129 and/or illumination device(s) 128 visualizing and/or illuminating the treatment site. Additionally or alternatively, inner cap 134 and/or outer cap 132 may include markings (e.g., fluoroscopic, radiopaque, etc. markings) to assist with the visualization of outer cap 132 and/or inner cap 134 during, for example, a fluoroscopic procedure.

Additionally or alternatively, one or more surfaces of outer cap 132 and/or inner cap 134 may be at least partially coated with any biocompatible material commonly known in the art (e.g., silicone-based lubricants, coatings, gels, fluids, etc.). For example, coating one or more outer surfaces or portions of outer cap 132 and/or one or more outer surfaces of inner cap 134 (e.g., a distal face of distal wall 136) may facilitate the insertion, positioning, and/or removal of end cap 130 into the subject. Similarly, coating one or more inner surfaces or portions of inner cap 134 may facilitate the insertion, positioning, and/or removal of end cap 130 onto distal portion 125C of endoscope 125 (shown in FIG. 1). Additionally or alternatively, coating one or more inner surfaces or portions of outer cap 132 and/or coating one or more outer surfaces or portions of inner cap 134 may facilitate the extension and/or retraction of inner cap 134 from outer cap 132.

A longitudinal length of inner cap 134 may range from approximately 1 centimeters to approximately 3 centimeters, for example, approximately 2 centimeters. Accordingly, a longitudinal length of outer cap 132 may range from approximately 1 centimeters to approximately 3.5 centimeters, for example, approximately 2.2 centimeters. However, it is understood that outer cap 132 and inner cap 134 may include various other shapes, sizes, and/or lengths than those shown and described herein.

In some embodiments, inner cap 134 may include an overall outer diameter of approximately 10 millimeters to approximately 20 millimeters, for example, approximately 15 millimeters. Intermediate portion 131 of inner cap 134 may have an outer diameter of approximately 9 millimeters to approximately 18 millimeters, for example, approximately 10 millimeters. Accordingly, proximal wall 135 and distal wall 136 may extend radially outward from intermediate portion 131 by approximately 1 millimeter to approximately 10 millimeters, for example, approximately 5 millimeters. In some aspects, outer cap 132 and/or inner cap 134 may have a lateral cross-sectional shape, such as, for example, an oval, circle, square, rectangle, star, or any shape commonly known in the art.

As mentioned above, inner cap 134 further comprises lumen 138. Lumen 138 may be sufficiently sized such that at least a portion of lumen 127 (shown in FIG. 2B) of endoscope 125 is in fluid communication with lumen 138. Lumen 138 may also be sized such that inner cap 134 does not cover or otherwise interfere with one or more visualization device(s) 129 and/or one or more illumination device (s) 128. By way of example only, in some embodiments, lumen 138 of inner cap 134 may include an inner diameter of approximately 7 millimeters to approximately 15 millimeters, for example, approximately 10.5 millimeters to approximately 12 millimeters. The inner diameter of lumen 138 may be the same along an entire longitudinal length of inner cap 134. In alternative examples (not shown), the inner diameter of lumen 138 may vary along the longitudinal length. For example, the inner diameter of lumen 138 may increase along the longitudinal length such that the inner diameter is greater on a distal portion of inner cap 134 as compared to a distal portion of lumen 138. Alternatively, the inner diameter of lumen 138 may decrease along the longitudinal length such that the inner diameter is greater on a proximal portion of inner cap 134 as compared to a distal portion of inner cap 134. In some aspects, lumen 138 may have a lateral cross-sectional shape, such as, for example, an oval, circle, square, rectangle, star, or any shape commonly known in the art.

In some embodiments, outer cap 132 may include an overall outer diameter of approximately 12 millimeters to approximately 25 millimeters, for example, approximately 16 millimeters. Lumen 137 of outer cap 132 may include an inner diameter of approximately 10 millimeters to approximately 22 millimeters, for example, approximately 15.5 millimeters. In some aspects, outer cap 132 may have a lateral cross-sectional shape, such as, for example, an oval, circle, square, rectangle, star, or any shape commonly known in the art.

Figure 3A:
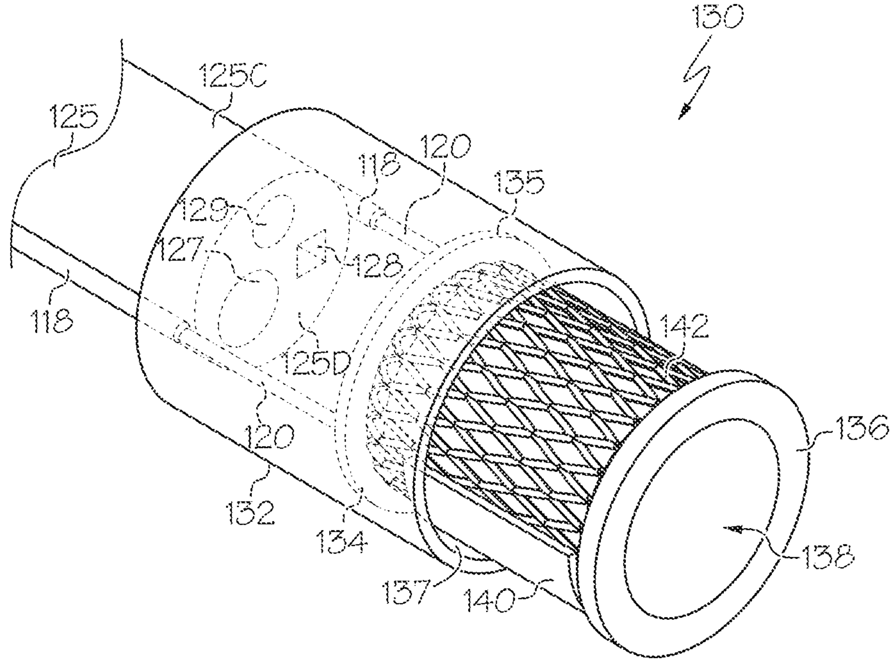
FIGS. 3A and 3B are perspective views of the distal end of the medical device at various steps of an exemplary procedure, according to aspects of this disclosure.
Figure 3B:
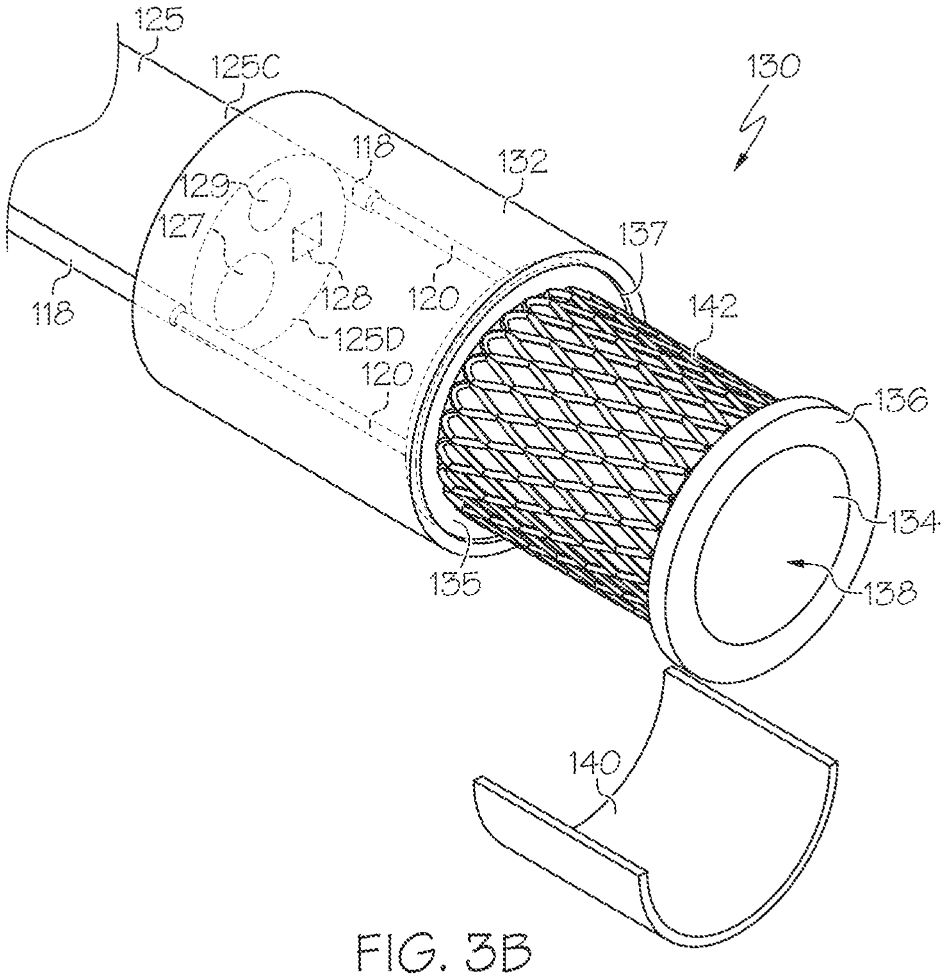

FIGS. 3A and 3B provide perspective views of end cap 130 with end cap 130 in various configurations. FIG. 3A illustrates end cap 130 in an intermediate position while transitioning between the first configuration (FIGS. 2A and 2B) and a second configuration (FIG. 3B). FIG. 3B illustrates end cap 130 in the second configuration. To transition end cap 130 from the first configuration to the second (e.g., actuated or extended) configuration, the user may actuate movable body 110 (shown in FIG. 1), for example, by moving one or more fingers in groove 110A. For example, the user may move one or more fingers in groove 110A distally to move movable body 110 distally, and thus transition end cap 130 from the first configuration to the second configuration. Actuating movable body 110 results in the actuation, or extension, of control element(s) 120. Accordingly, as control element(s) 120 are extended distally relative to one or more sheath element(s) 118, inner cap 134 may be extended distally relative to outer cap 132. For example, distal wall 136 of inner cap 134 may extend distally past distal end 132A of outer cap 132. As shown in FIG. 3B, however, at least a portion of proximal wall 135 may remain proximal to distal end 132A of outer cap 132 in the second configuration. For example, in some embodiments, outer cap 132 may include a feature (not shown) projecting radially inward from a surface of lumen 137. The feature (not shown) may catch or abut against proximal wall 135, thereby helping to prevent inner cap 134 (e.g., proximal wall 135) from extending distally beyond distal end 132A of outer cap 132. Inner cap 134 may also be positioned in one or more intermediate positions. For example, inner cap 134 can be partially extended distally relative to outer cap 132.

During and/or after the transition from the first configuration to the second configuration, lumen 127 of endoscope 125 may remain in fluid communication with lumen 138 of inner cap 134. Similarly, during and/or after the transition from the first configuration to the second configuration, neither inner cap 134 nor outer cap 132 cover or otherwise interfere with one or more visualization device(s) 129 and/or one or more illumination device(s) 128. Accordingly, the user may be able to visualize the target tissue or other aspects of the treatment site during the entirety of the procedure.

As inner cap 134 is extended distally relative to outer cap 132, patch 140 is also extended distally. Additionally, as inner cap is extended distally, support structure 142 may expand or otherwise be actuated. Support structure 142 may expand (e.g., radially outward), at least in part, due to the shape-memory characteristics previously described. For example, as inner cap 134 is extended, support structure 142 may no longer be confined by the walls defining lumen 137 of outer cap 132. Accordingly, the external walls of support structure 142 may push radially outward, or radially away from inner cap 134. As the external walls of support structure 142 are pushed radially outwards, patch 140 may be pushed against or toward the target tissue and/or otherwise be released or deployed from end cap 130 to the treatment site. In alternative configurations (not shown), one or more auxiliary medical devices may be delivered through lumen 127 of endoscope 125 to assist in positioning or repositioning in patch 140 once it is released or deployed from end cap 130.

Inner cap 134 may also be retracted within outer cap 132, for example, by retracting control element(s) 120. Control element(s) 120 may be retracted by, for example, moving one or more fingers in groove 110A, shown in FIG. 1, in an opposite direction as before, for example, proximally. Inner cap 134 may be retracted or returned to the first configuration, shown in FIGS. 2A and 2B. Additionally, as inner cap 134 is retracted within outer cap 132, support structure 142 may return to the original shape and/or size. For example, support structure 142 may retract (e.g., radially inward), as the walls defining lumen 137 of outer cap 132 confine support structure 142.

Patch 140 may be a biodegradable and/or biocompatible patch of any suitable shape and any suitable dimension, e.g. based on the nature of the target tissue site. Patch 140 may have any shape such as, e.g., approximately square, approximately rectangular, rounded square, rounded rectangle, ovate, circular, among other possible shapes. In some examples, the thickness of the patch may be on the order of millimeters, e.g. ranging from about 0.1 mm to 5.0 mm or, more specifically, from about 0.7 mm to about 2.0 mm. Patch 140 may be sufficiently sized to cover the target tissue with a margin for resection. Thus, patch 140 can come in many sizes to accomplish such a task. Moreover, patch 140 may be of any suitable color, including clear, and material, e.g., nettings, cloths, polysaccharides (chitosan, cellulose, starch, alginates, etc.) that may be further modified with synthetic biocompatible materials (pHEMA, PGA, PLA, PCA, PEG, etc.). Additionally, for example, patch 140 may be comprised of polypropylene, polyester, ePTFE, and/or silicone. Patch 140 may be adhered to the target tissue using materials commonly known in the art, such as, for example fibrin glue, hydrogel, and/or cyanoacrylate. Alternatively or additionally, patch 140 may be comprised of or dosed with agents to prevent the shedding of cells from the target tissue or to treat the treatment site. Alternatively or additionally, patch 140 may comprise one or more hemostatic material(s) or agent(s). In some configurations, the hemostatic material (s) or agent(s) may be applied to patch 140 after patch 140 is coupled, or adhered, to the target tissue.

Patch 140 may be pliable and bendable. For example, patch 140 may be formed into a planar film, sheet, or disc capable of being folded, crimped, or otherwise manipulated into a temporary non-planar configuration within a confined space or when other forces act on patch 140. For example, patch 140 may be folded, curved, or crimped between inner cap 134 and outer cap 132 of end cap 130 for suitable delivery to the target tissue. However, once at least a portion of inner cap 134 is extended distally beyond outer cap 132, thereby actuating support structure 142, patch 140 may be released from support structure 142. Accordingly, patch 140 may recover its original planar, or other expanded, configuration.

Patch 140 may be substantially dry during delivery to a treatment site. For example, one or more proximal portion(s) of outer cap 132 and inner cap 134 and one or more distal portion(s) of outer cap 132 and inner cap 134 may form a seal, or a liquid-tight barrier, to prevent bodily fluids from contacting patch 140 before delivery or deployment. In some examples herein, patch 140 may be moistened during delivery or shortly following release from end cap 130. For example, patch 140 may be exposed to water or another fluid via lumen 127 of endoscope 125 and/or through contact with bodily fluids or humidity inside the body of the subject. In some embodiments, for example, lumen 127 of endoscope 125 may be in fluid connection with a fluid supply connector (not shown) or a similar structure (e.g., a port). When exposed to moisture, patch 140 may absorb the fluid, causing patch 140 to swell or expand. For example, patch 140, when dry, may be substantially paper-like, and, when wet, may take on a more jelly-like consistency. According to some aspects of this disclosure, moistening patch 140 may assist in its application to tissue.

In some examples herein, patch 140 comprises an adhesive, for example, to assist in applying the patch to tissue and/or maintaining the patch in place after application, and/or to assist in delivery of patch 140 to the treatment site. The adhesive may be disposed on a surface, or a side, of patch 140 opposite a surface, or a side, of patch 140 abutting support structure 142. The adhesive may be disposed on the surface or the side of patch 140 in certain discrete locations or on the entirety of the surface. Adhesives suitable for this disclosure may be natural, for example, comprising a natural polymer or derived from a natural polymer, or synthetic. Exemplary adhesives include, but are not limited to, gelatin (including, e.g., thrombin/gelatin), fibrin (e.g., fibrin glue), cyanoacrylate, polyethylene glycol (PEG), and albumin (including, e.g., albumin glutaraldehyde). The adhesive may be at least partially resorbable by a subject's body.

The choice of adhesive may be at least partially based on the desired adhesion strength, bioresorbable properties, and/or the nature of the treatment site to which patch 140 is being applied. For example, a relatively stronger adhesive may be desired for a patch 140 comprising an extracellular matrix (ECM) than for a patch 140 comprising chitosan, which has natural bioadhesive properties. Further, for example, a patch 140 intended for application to a relatively large wound, tumor, or defect site, may comprise adhesive to further assist with securing patch 140 to the tissue. Patch 140, according to this disclosure, may comprise adhesive applied to one area or two or more areas, for example, opposing ends of patch 140. Alternatively or additionally, the adhesive may be applied within the perimeter of patch 140, leaving a center portion of patch 140 without adhesive. In some examples, patch 140 does not include an adhesive. Accordingly, as patch 140 is released from support structure 142, patch 140 may be adhered to the target tissue or otherwise positioned at the treatment site.

Figure 4:
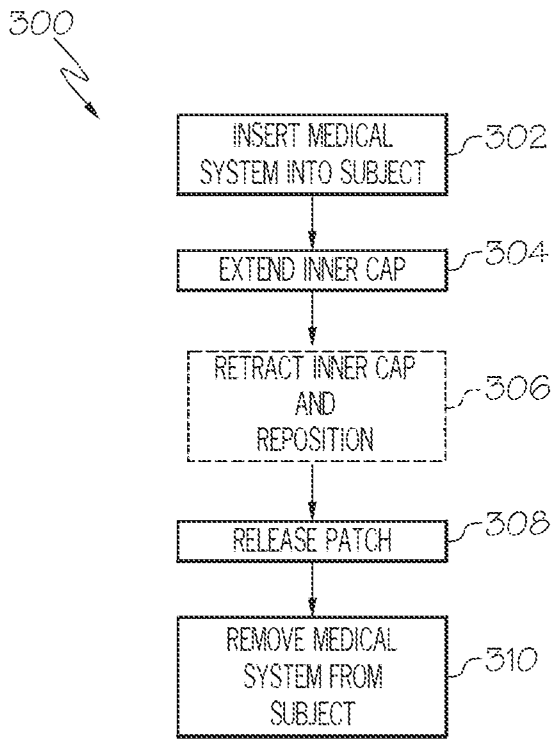
FIG. 4 is a flow diagram of an exemplary method, according to aspects of this disclosure.

FIG. 4 is a flow diagram of an exemplary method 300 that one or more users may perform with any of the medical systems, devices, or portions of systems discussed herein, for example, medical system 100. In a first step 302 of method 300, medical system 100 (e.g., a distal portion of medical system 100) may be inserted into the subject, for example, through a natural orifice or an incision. Medical system 100 may include, for example, medical device 102 and endoscope 125. Medical device 102 may further include handle 103 and end cap 130. First step 302 may also include coupling end cap 130 to distal portion 125C of endoscope 125 prior to inserting medical system 100 into the subject. First step 302 may further include deflecting and/or positioning distal portion 125C of endoscope 125 (e.g., via knobs, levers, dials, etc.).

Once medical system 100 is in the desired position, a second step 304 includes extending inner cap 134, for example, by manipulating movable body 110 of handle 103 relative to stationary body 112 (e.g., distally relative to stationary body 112). Moving movable body 110 of handle 103 relative to stationary body 112 may extend or otherwise actuate inner cap 134 relative to outer cap 132.

In an optional step 306 of method 300, for example, before patch 140 is released from inner cap 134, the user(s) may retract, or deactivate, inner cap 134 and reposition end cap 130 within the subject. For example, the user(s) may move endoscope 125 proximally or distally and/or move control element(s) 120 via handle 103. Optional step 306 may also include deflecting and/or positioning distal portion 125C of endoscope 125 (e.g., via knobs, levers, dials, etc.)

In a step 308, inner cap 134 is fully extended, or actuated, and patch 140 is released from inner cap 134. Inner cap 134 may be extended, or actuated, for example, by advancing movable body 110 distally relative to stationary body 112. Movable body 110 may control the movement (e.g., extension or retraction) of control element(s) 120 coupled to end cap 130. Thus, for example, when control element(s) 120 is/are advanced distally, inner cap 134 is extended, or actuated. Movable body 110 may include, for example, visual or physical indicator(s) 109. Indicator(s) 109 may include, for example, indentations, raised surfaces, markings, etc. Indicator(s) 109 may physically or visually indicate the actuation or extension of end cap 130. Outer cap 132 may include a feature projecting radially inward to prevent inner cap 134 from extending distally beyond distal end 132A of outer cap 132.

Once patch 140 is released, the user(s) may remove medical system 100 from the subject, in a step 310. For example, medical system 100 may be removed by pulling endoscope 125 proximally through the natural orifice or incision. Once medical system 100 is removed, method 300 may be repeated, for example, with a second end cap 130 or the same end cap 130 with a new patch 140. Before, during, or after removal of medical system 100, the user(s) may retract inner cap 134 within outer cap 132.

Figure 5A:
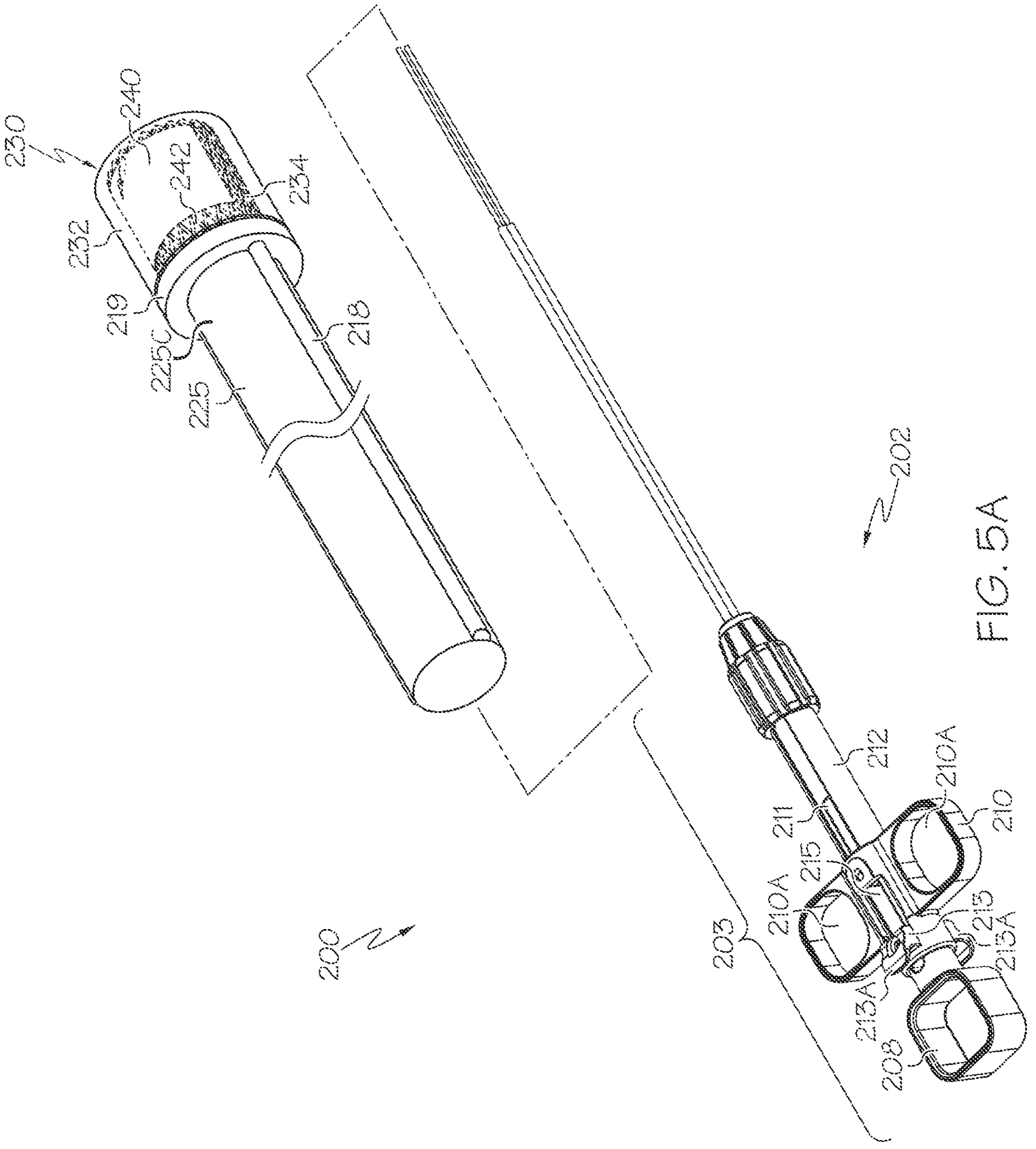
FIGS. 5A and 5B are perspective views of a distal end portion of an alternative exemplary medical device in a retracted configuration (FIG. 5A) and in an extended configuration (FIG. 5B) relative to an endoscope, according to aspects of this disclosure.
Figure 5B:
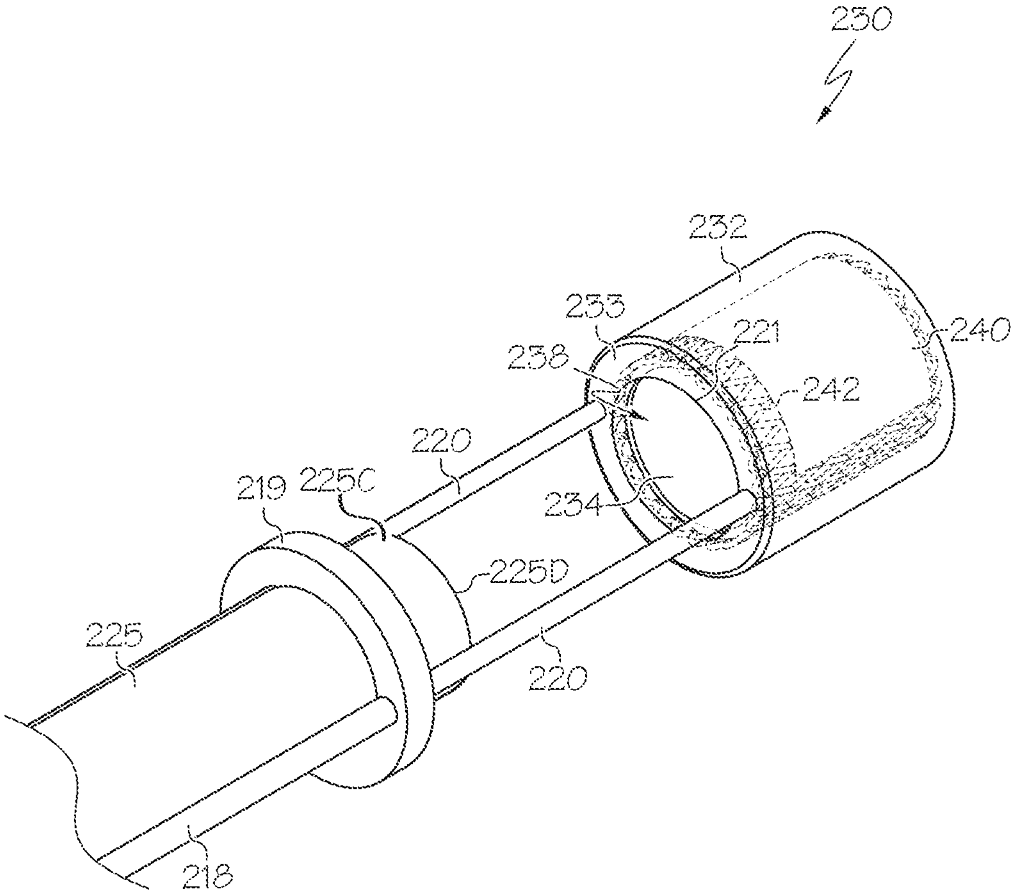

FIGS. 5A and 5B illustrate perspective views of an alternative medical system 200 in a first, e.g., retracted, configuration (FIG. 5A) and in a second, e.g., extended, configuration (FIG. 5B). Medical system 200 may include a medical device 202 and an endoscope 225. Medical device 202 may include a handle 203 and end cap 230. End cap 230 may have any of the characteristics of end cap 130, except as described below. Similarly, handle 203 may have any of the characteristics of handle 103, except as described below.

Handle 203 may include a first movable body 210 and a stationary body 212. For example, movement of first movable body 210 relative to stationary body 212 may control the movement (e.g., extension or retraction) of one or more control element(s) 220 (shown in FIG. 5B), for example, control wire(s), and thus control element(s) 220 may control the movement (e.g., extension or retraction) of one or more portions of end cap 230. First movable body 210 may partially surround a portion of stationary body 212, and a portion of first movable body 210 may at least partially extend into a handle slot 211. Handle slot 211 may extend longitudinally through at least a portion of stationary body 212 of handle 203. In some aspects, although not shown, handle 203 may include one or more biasing elements (e.g., one or more springs), for example, such that distal movement of first movable body 210 relative to stationary body 212 is biased proximally. In these aspects, when the user releases a distal pressure or force on first movable body 210, the one or more biasing elements may bias first movable body 210 proximally. Moreover, at least a portion of first movable body 210 may be coupled to (e.g., directly or indirectly) or otherwise connected to control element(s) 220.

First movable body 210 may include one or more finger holes 210A extending radially outward from first movable body 210. Accordingly, movement of the user's fingers (i.e. relative to the user's thumb in finger ring 208) may control the position of first movable body 210 relative to stationary body 212, and thus the movement of control element(s) 220 and/or one or more portions of end cap 230. Additionally or alternatively, first movable body 210 may be formed similarly to movable body 110 of FIG. 1. For example, first movable body 210 may comprise one or more reduced diameter sections or grooves to facilitate the user's grip of movable body 110.

Handle 203 may also include a second movable body 213, for example, movably mounted on or otherwise coupled to first movable body 210. Movement of second movable body 213 relative to first movable body 210 may control the movement (e.g., extension or retraction) of one or more activation wire(s) 222, for example, and thus activation wire(s) may control the movement (e.g., extension or retraction) of one or more portions of end cap 230. A portion of second movable body 213 may at least partially extend into a handle slot 215. Handle slot 215 may extend longitudinally through at least a portion of first movable body 210 of handle 203. In some aspects, although not shown, one or more portions of handle 203 (e.g., first movable body 210) may include one or more biasing elements (e.g., one or more springs), for example, such that distal movement of second movable body 213 relative to first movable body 210 is biased proximally. In these aspects, when the user releases a distal pressure or force on second movable body 213, the one or more biasing elements may bias second movable body 213 proximally, for example, to the position shown in FIG. 5A. Moreover, at least a portion of second movable body 213 may be coupled to (e.g., directly or indirectly) or otherwise connected to activation wire(s) 222.

Second movable body 213 may include one or more tabs, or features, 213A, which may help facilitate the user's grip and/or movement of second movable body 213. Accordingly, movement of the user's fingers controls the position of second movable body 213 relative to first movable body 210, and thus the movement of activation wire(s) 222 and/or one or more portions of end cap 230. For example, the user may use one or more fingers of the user's other hand to grip and/or move second movable body 213.

Although not shown, stationary body 212, first movable body 210, and/or second movable body 213 may include one or more visual or physical indicator(s) similar to the one or more visual or physical indicator(s) 109 of FIG. 1. The indicator(s) may include, for example, indentations, raised surfaces, markings, etc. The indicator(s) may physically or visually indicate the actuation or extension of end cap 230. For example, as first movable body 210 is advanced distally relative to stationary body 212, thus actuating at least a portion of end cap 230, first movable body 210 may have to overcome, for example, the indicator(s) on stationary body 212. The indicator(s) on stationary body 212 may signal to the user that a first portion of end cap 230 has been actuated, or is in an extended position. Similarly, as second movable body 213 is advanced distally relative to first movable body 210, thus actuating at least a second portion of end cap 230, second movable body 213 may have to overcome, for example, the indicator(s) on first movable body 210. Additionally or alternatively, the user may utilize markings on handle 203 or other visual indicators to determine a status, position, actuation status, etc. of one or more portions of end cap 230. The indicator(s) on the first movable body 210 may signal to the user that a second portion of end cap 230 has been actuated, or is in an extended position Endoscope 225 may have any of the characteristics of endoscope 125. Coupler ring 219 may be coupled to an external surface of an endoscope 225 by techniques such as, for example, an adhesive, a mechanical fit, a snap fit, a press fit, a weld, or any other techniques commonly known in the art. Coupler ring 219 may, for example, provide an anchor for end cap 230 to endoscope 225. Coupler ring 219 may be formed of a rigid or semi-rigid material (e.g. stainless steel, titanium, polypropylene plastic, high-density polyethylene plastic, acrylic, aluminum, brass, etc. Coupler ring 219 may be sufficiently sized to receive, for example, a distal end 225C of endoscope 225. In the first (e.g., retracted) configuration, as shown in FIG. 5A, a proximal face of an outer cap 232 may be adjacent to, or touch, a distal face of coupler ring 219.

Similar to the previous embodiment, end cap 230 may comprise an outer cap 232 and an inner cap 234 movable relative to outer cap 232. A support structure 242 may extend partially or completely around a portion of inner cap 234, for example, between outer cap 232 and inner cap 234. Inner cap 234 may include a lumen 238 extending from a proximal end to a distal end of inner cap 234. Although not shown, inner cap 234 may include a proximal wall and/or a distal wall, similar to proximal wall 135 and distal wall 136 of the previous embodiment. A patch 240 may be positioned on an external surface of a support structure 242. In the first configuration, patch 240 may be confined between inner cap 234 and outer cap 232, for example, radially external to support structure 242.

As shown in FIG. 5B, control element(s) 220 may extend through coupler ring 219 and be coupled to a proximal face 233 of outer cap 232. Proximal face 233 may include an opening 221, for example, to receive a distal portion of endoscope 225 in the first configuration, as shown in FIG. 5A, and/or to permit fluids to flow through outer cap 232 and lumen 238 of inner cap 234 in the second configuration, as shown in FIG. 5B.

By moving first movable body 210, shown in FIG. 5A, distally within handle 203, control element(s) 220 may be extended distally relative to control sheath(s) 218. Accordingly, when control element(s) 220 are extended distally relative to control sheath(s) 218, outer cap 232 and inner cap 234 are extended distally relative to a distal end 225D of endoscope 225. For example, in the second configuration, outer cap 232 and inner cap 234 are extended approximately 1 centimeter to approximately 4 centimeters, for example, approximately 2 centimeters, beyond distal end 225D. In the second configuration, patch 240 may remain confined between inner cap 234 and outer cap 232, for example, radially exterior to support structure 242.

Figure 6A:
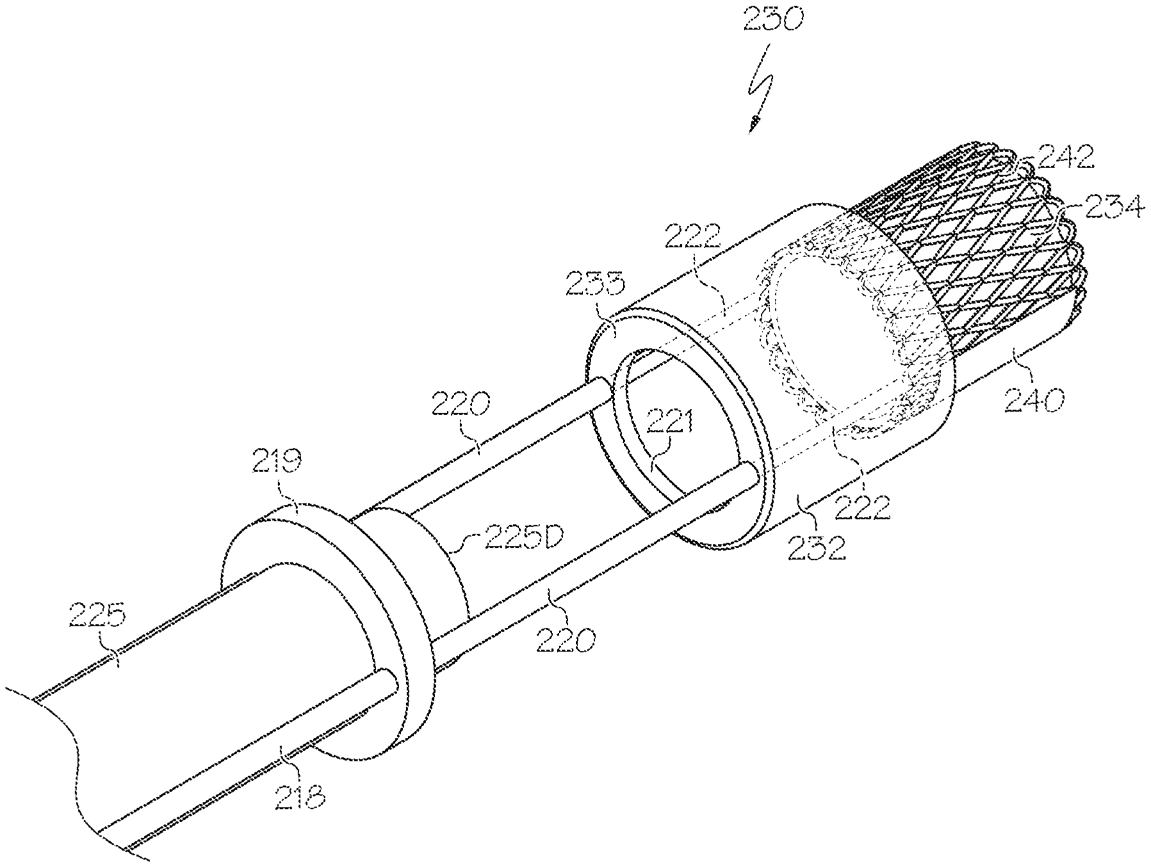
FIGS. 6A and 6B are perspective views of the distal end portion of the alternative medical device at various steps of an exemplary procedure, according to aspects of this disclosure.
Figure 6B:
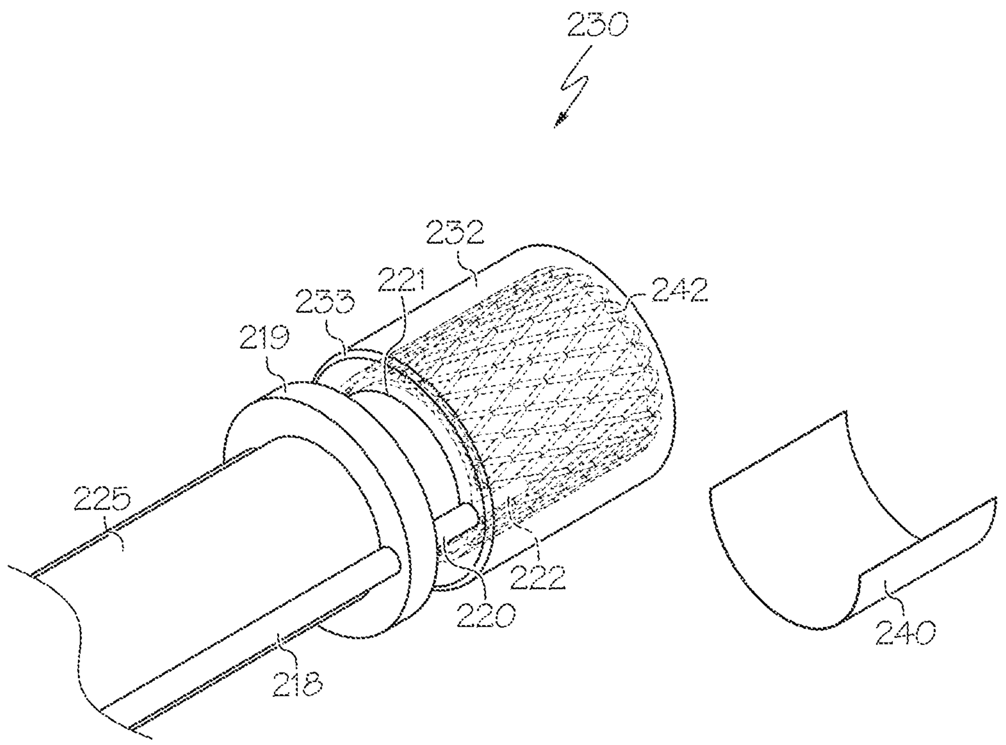

FIGS. 6A and 6B illustrate perspective views of medical system 200 in a third configuration (FIG. 6A) and a fourth configuration (FIG. 6B). For example, in the third configuration, inner cap 234 of end cap 230 is extended distally beyond a distal end of outer cap 232. For example, in the third configuration, one or more activation wire(s) 222 is/are extended distally relative to control element(s) 220. Activation wire(s) 222 may be radially within control element(s) 220. Activation wire(s) 222 may be coupled to a proximal portion of inner cap 234. Additionally or alternatively, activation wire(s) 222 may be coupled to an intermediate and/or a distal portion of inner cap 234. Accordingly, extending activation wire(s) 222 distally beyond control element(s) 220 extends inner cap 234 relative to outer cap 232.

The extension of activation wire(s) 222 may be accomplished by, for example, moving second movable body 213, shown in FIG. 5A, distally relative to first movable body 210. Accordingly, extending inner cap 234 relative to outer cap 232 results in the expansion, or actuation of support structure 242. First movable body 210, may comprise one or more indicator(s), e.g., adjacent to slot 215, that corresponds to a position of second movable body 213 in slot 215. Accordingly, the indicator(s) may correspond to a position at which inner cap 234 is positioned relative to outer cap 232 such that the support structure can expand radially outward.

Support structure 242 may be expanded in a similar manner as described above with respect to support structure 142 of the first embodiment. For example, as inner cap 234 is extended, support structure 242 is no longer confined by the internal walls of outer cap 232. Accordingly, support structure 242 may push radially outward, or away from inner cap 234. As the external walls of support structure 242 are pushed radially outwards, patch 240 may be pushed against the target tissue and/or otherwise released or deployed, as shown in FIG. 6B.

As shown in FIG. 6B, once patch 240 is released or deployed, inner cap 234 is retracted, or pulled proximally, within outer cap 232, thereby retracting activation wire(s) 222 within control element(s) 220. Additionally, outer cap 232 is retracted or pulled proximally, such that proximal face 233 is adjacent to or touching the distal face of coupler ring 219, similar to the first configuration. A distal portion of endoscope 225 may be received by opening 221 of outer cap 232. In this configuration, control element(s) 220 may be retracted within control sheath(s) 218.

Medical system 200 may also be used to perform one or more steps of method 300, except as described below. For example, once medical system 200 is inserted into the body, additional steps may be required to extend outer cap 232 and inner cap 234 to the second configuration, shown in FIG. 5B. Once in the desired position, inner cap 234 may be extended to release patch 240. Similar to the previous embodiment, before patch 240 is released, inner cap 234 and/or endoscope 225 may be retracted or repositioned one or more times in order to reposition inner cap 234 within the subject. However, once patch 240 is released, the user(s) may retract inner cap 234 within outer cap 232 and retract outer cap 232 relative to endoscope 225, as shown in FIG. 6B. Medical system 200 may then be removed from the subject.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

We claim:

1. A medical device, comprising:

a handle, wherein the handle includes a movable body and a stationary body;

an end cap, the end cap comprising an inner cap and an outer cap, wherein the inner cap is coupled to the movable body by a control element such that movement of the movable body relative to the stationary body extends the inner cap relative to the outer cap; and a patch disposed between the inner cap and the outer cap such that movement of the inner cap relative to the outer cap at least partially deploys the patch, wherein the inner cap includes a proximal wall and a distal wall extending radially outward from the inner cap, wherein, in a first configuration, an outer edge of the distal wall of the inner cap abuts an inner edge of the outer cap, and, wherein, in a second configuration, the outer edge of the distal wall of the inner cap is distal to the inner edge of the outer cap.

2. The medical device of claim 1, further comprising a support structure partially surrounding a portion of the inner cap, and wherein distal movement of the inner cap relative to the outer cap results in the support structure expanding.

3. The medical device of claim 2, wherein the support structure includes a woven shape-memory material.

4. The medical device of claim 1, wherein the control element is moveably disposed within a lumen of a sheath.

5. The medical device of claim 4, wherein the sheath is coupled to the outer cap.

6. The medical device of claim 1, wherein the end cap is removably coupled to an endoscope by one or more fasteners, adhesives, or a friction fit.

7. The medical device of claim 1, wherein the inner cap includes a lumen extending from a proximal end to a distal end.

8. The medical device of claim 1, wherein the patch includes an adhesive on a side of the patch facing away from the inner cap.

9. The medical device of claim 1, wherein the patch includes a hemostatic agent.

10. The medical device of claim 1, wherein at least a portion of the end cap is transparent.

11. The medical device of claim 1, wherein a proximal end of the end cap is configured to receive a distal end of a scope.

12. The medical device of claim 1, wherein the patch is a film, sheet, or disc.

13. A medical device, comprising:

an end cap, the end cap comprising an inner cap and an outer cap, wherein the inner cap includes a lumen extending from a proximal end to a distal end of the inner cap;

an expandable structure, the expandable structure partially surrounding a portion of the inner cap; and a patch positioned around the expandable structure;

wherein, in a first configuration, the inner cap is disposed within the outer cap and the patch is disposed between the portion of the inner cap and a portion of the outer cap, and, in a second configuration, at least a distal portion of the inner cap is distal to the outer cap and the patch is released.

14. The medical device of claim 13, wherein the expandable structure includes a woven shape-memory material.

15. The medical device of claim 13, wherein the inner cap includes a proximal wall and a distal wall extending radially outward from the inner cap, wherein, in the first configuration, an outer edge of the distal wall of the inner cap abuts an inner edge of the outer cap, and, wherein, in the second configuration, the outer edge of the distal wall of the inner cap is distal to the inner edge of the outer cap.

16. The medical device of claim 13, wherein at least a portion of the end cap is transparent.

17. The medical device of claim 13, wherein a diameter of the lumen at a proximal portion of the inner cap is smaller than the diameter of the lumen at a distal portion of the inner cap.

18. A medical device, comprising:

a handle, wherein the handle includes a movable body and a stationary body; and an end cap, the end cap comprising:

an outer cap; and an inner cap movable relative to the outer cap via movement of the movable body relative to the stationary body, the inner cap including:

a proximal wall;

a distal wall;

an intermediate portion disposed therebetween, wherein each of the proximal wall and the distal wall extend radially outward relative to the intermediate portion, and wherein an outer edge of the distal wall of the inner cap is complementary to an inner edge of the outer cap; and a support structure extending around a radially external surface of the intermediate portion, and wherein, in a first configuration, a patch is disposed between the intermediate portion of the inner cap and the outer cap, and wherein, in a second configuration, (1) the inner cap is moved relative to the outer cap, and (2) the patch is released from the intermediate portion of the inner cap.

19. The medical device of claim 18, wherein the support structure extends between the proximal wall and the distal wall.

20. The medical device of claim 18, wherein the inner cap defines a lumen extending from a proximal end to a distal end of the inner cap.

* * * * *